United States Patent
Croud et al.

(10) Patent No.: US 10,267,740 B2
(45) Date of Patent: *Apr. 23, 2019

(54) TRACER AND METHOD OF IDENTIFYING TRACER IN PRODUCT

(71) Applicant: JOHNSON MATTHEY PUBLIC LIMITED COMPANY, London (GB)

(72) Inventors: Vincent Brian Croud, Sheffield (GB); Elizabeth Ruth Egginton, Thirsk North (GB); Clive Anthony Marchant, Billingham (GB); Duncan William John McCallien, Darlington (GB); Alistair McInroy, Glasgow (GB); David Eustace, Glasgow (GB); Graeme McNay, Glasgow (GB)

(73) Assignee: Johnson Matthey Public Limited Company, London (GB)

( * ) Notice: Subject to any disclaimer, the term of this patent is extended or adjusted under 35 U.S.C. 154(b) by 163 days.

This patent is subject to a terminal disclaimer.

(21) Appl. No.: 14/389,104

(22) PCT Filed: Mar. 28, 2013

(86) PCT No.: PCT/GB2013/050852
§ 371 (c)(1),
(2) Date: Sep. 29, 2014

(87) PCT Pub. No.: WO2013/144657
PCT Pub. Date: Oct. 3, 2013

(65) Prior Publication Data
US 2015/0077745 A1    Mar. 19, 2015

(30) Foreign Application Priority Data

Mar. 30, 2012    (GB) .................................... 1205748.5
Mar. 30, 2012    (GB) .................................... 1205779.0

(51) Int. Cl.
*G01N 21/65*    (2006.01)
*G01N 21/01*    (2006.01)
*G01N 21/85*    (2006.01)

(52) U.S. Cl.
CPC ........... *G01N 21/658* (2013.01); *G01N 21/01* (2013.01); *G01N 21/85* (2013.01)

(58) Field of Classification Search
CPC ............................. G01N 21/658; G01N 21/65
See application file for complete search history.

(56) References Cited

U.S. PATENT DOCUMENTS 4,802,761 A * 2/1989 Bowen .................. G01N 21/03
356/246
4,924,710 A    5/1990 Inada et al.
(Continued)

FOREIGN PATENT DOCUMENTS

CN    1038159    12/1989
CN    1092864    9/1994
(Continued)

OTHER PUBLICATIONS

International Search Report, dated Jul. 9, 2013, from corresponding PCT application.
(Continued)

*Primary Examiner* — Kara E. Geisel
*Assistant Examiner* — Rufus L Phillips
(74) *Attorney, Agent, or Firm* — BakerHostetler

(57) ABSTRACT

A method of detecting a tracer compound dissolved in a liquid composition via surface-enhanced spectroscopy includes the steps of:
  a. optionally, diluting the liquid composition or the separated liquid by mixing with a diluent liquid;
  b. bringing a sample of the separated liquid into contact with, a spectroscopy-enhancing surface including gold, silver or copper;

(Continued)

c. obtaining a Raman spectrum from the sample; and
d. calculating, from the spectrum, the concentration of the tracer in the sample relative to the concentration of a second component of the composition.

13 Claims, 4 Drawing Sheets

(56) References Cited

U.S. PATENT DOCUMENTS

| | | | |
|---|---|---|---|
| 6,127,120 A * | 10/2000 | Graham et al. | 435/6.14 |
| 6,514,767 B1 * | 2/2003 | Natan | 436/166 |
| 7,869,030 B2 * | 1/2011 | Zhong et al. | 356/301 |
| 8,344,334 B2 * | 1/2013 | Coker et al. | 250/459.1 |
| 8,828,729 B1 * | 9/2014 | Natan et al. | 436/56 |
| 2003/0049850 A1 * | 3/2003 | Golden | C25D 3/38 436/56 |
| 2004/0179195 A1 * | 9/2004 | Su | B82Y 20/00 356/301 |
| 2005/0250091 A1 * | 11/2005 | Maier et al. | 435/4 |
| 2005/0266583 A1 | 12/2005 | Farquharson et al. | |
| 2005/0280817 A1 * | 12/2005 | Horchner | G01J 3/2803 356/318 |
| 2008/0158558 A1 * | 7/2008 | Li | C12Q 1/42 356/301 |
| 2013/0271758 A1 * | 10/2013 | Marchant et al. | 356/301 |

FOREIGN PATENT DOCUMENTS

| | | | |
|---|---|---|---|
| WO | 9412874 | 6/1994 | |
| WO | 99/00666 A1 | 1/1999 | |
| WO | 0171353 | 9/2001 | |
| WO | WO 2007129055 A1 * | 11/2007 | F01N 3/2066 |
| WO | 2008/019161 A2 | 2/2008 | |
| WO | 2010/057212 A1 | 5/2010 | |
| WO | 2012/052779 A1 | 4/2012 | |

OTHER PUBLICATIONS

English translation of Chinese Office Action dated Apr. 29, 2016, in corresponding Chinese Application No. 201380018294.4, dated Apr. 29, 2016.

* cited by examiner

TRACER AND METHOD OF IDENTIFYING TRACER IN PRODUCT

BACKGROUND OF THE INVENTION

Field of the Invention

The invention concerns a tracer and a method of detecting tracer compounds in product compositions. In particular the method concerns the detection of tracer compounds in complex product compositions by means of surface-enhanced spectroscopy techniques.

Description of the Related Art

It is well-known to add distinctive tracer compounds to high-value products in order to provide a means for identifying fake products and also to determine whether a genuine product has been adulterated, for example by dilution. The tracer compound is normally added in very low concentrations and consequently the use of sensitive analytical methods is required in order to detect the tracer compound, and also to measure a change in the concentration of the tracer compound compared with the concentration at which it was added. Surface enhanced spectroscopy (SES) is one such method of determining an analyte at very low concentrations. The use of SES for the detection of tracer compounds in liquid products is described, for example, in WO2008/019161 which concerns a method of fuel identification with surface enhanced Raman spectroscopy (SERS) tags. This method includes the association of a substance having a known Raman spectrum with a quantity of fuel. In one embodiment, a SERS active dye including a Raman active reporter compound may be mixed with a quantity of fuel. The process of identifying the fuel may then include mixing a sample of the fuel with a colloid of Raman enhancing metal particles and then acquiring the Raman spectrum of the Raman active reporter compound associated with the tracer. Alternatively, a portion of the sample may be associated with a SERS active substrate. The principle of detecting a SERS-active tracer compound in a liquid such as fuel by association with colloidal metal particles or a SERS substrate should, in theory, be applicable to other liquid products. We have found, however, that many products present problems which cannot be overcome by simply applying the simple methodology in WO2008/019161. Certain properties of liquid products, such as their viscosity, optical transparency or composition may inhibit the interaction of a tracer compound with the surface of the enhancing metal colloid or substrate or otherwise interfere with the collection of SERS spectra from the tracer compound. It is an object of the present invention to provide a method of identifying tracer compounds which may overcome at least some of the problems encountered with the prior art.

SUMMARY OF THE INVENTION

According to the invention, we provide a method of identifying a liquid composition comprising at least one original liquid ingredient, said method comprising the steps of:
a) adding a tracer compound to a known liquid composition containing said at least one original liquid ingredient to form a tagged known liquid composition;
b) obtaining a sample of an unidentified liquid composition
c) optionally, diluting said sample of an unidentified liquid composition by mixing with a liquid;
d) contacting said, optionally diluted, sample of the unidentified liquid with a spectroscopy-enhancing surface comprising gold, silver or copper;
e) obtaining a Raman spectrum from the sample; and
f) calculating, from said spectrum, the concentration of the tracer relative to the concentration of said original liquid ingredient in the sample of the unidentified composition;
g) comparing the relative concentration calculated in f with the corresponding relative concentration of the tracer and original liquid ingredient of the tagged known liquid composition.

Surface enhanced spectroscopy includes those spectroscopic methods which are susceptible to enhancement when the molecules of the analyte are close to or adsorbed by a material having a plasmon enhancing surface. Preferred forms of SES include SERS (surface-enhanced Raman spectroscopy) and SERRS (surface-enhanced resonance Raman spectroscopy). Preferably, the Raman spectrum is a resonance Raman spectrum.

The liquid composition is normally a product such as a fuel, fuel additive, lubricant, biologically derived product such as a vegetable oil for example, diesel exhaust fluid, pesticide, paint, ink, medicine, or any other composition for which assurance as to its source and identity is required. These products may be the target of counterfeiting activity, leading to economic and other damage to the providers of genuine products and often also to the users of the counterfeit products.

The tracer is selected to be soluble in the liquid composition and to be susceptible to be detected by means of SES. Preferably the tracer compound is detectable at concentrations less than $10^{-4}$ M, especially less than $10^{-6}$ M, particularly preferably at concentrations $\leq 10^{-7}$ M. In order for the tracer to be detectable at these levels it must provide a high SES signal intensity in the composition using the method of the invention. By "high signal intensity" we mean that the signal produced by the tracer must be distinguishable from that of any other components of the composition. The tracer must be stable in the composition over time. By stable we mean that the SES signal of the tracer, measured using the method of the invention, must not vary significantly over a period of time during which the composition may be required to be identified. This period is typically several months or years, i.e. whilst the composition remains in the distribution chain. The tracer may, if required, impart a visual colour to the composition, although such colour may be masked in highly coloured or opaque compositions. Alternatively a silent tracer may be used, i.e. a tracer which does not affect the appearance of the liquid composition when viewed with the naked eye.

Suitable tracers include xanthene dyes, such as Rhodamine dyes (e.g Rhodamine 6G), fluorescein, eosins (e.g. Eosine Y and Eosine B) azo (and diazo) dyes such as Allura Red and tartrazine; coumarins (e.g. 5,6-benzopyran-2-one), thiazoles, oxazine and triarylmethanes.

These coloured dyes are especially suitable for SERRS analysis using visible laser lines. Other suitable compounds include, as non-limiting examples, non-coloured compounds such as BPET (trans-1,2-bis(4-pyridyl)-ethylene and quinoline.

The liquid composition may optionally be separated to provide a liquid fraction containing the dissolved tracer compound and solid components of the composition (if any such are present).

This step may be done if solids present are found to interfere with the spectroscopy measurement, for example if they render the liquid composition too opaque for a meaningful spectrum to be obtained. The separation of the liquid containing the dissolved tracer compound from solids present in the composition may be carried out by any suitable means known to the skilled person. Such methods include filtration and centrifugation. If using filtration it is important to use a filtration method and materials which are not likely to affect the concentration of the tracer compound in the liquid filtrate. This can be achieved by selecting a filter medium to which the tracer compound does not adsorb or which does not absorb any components of the liquid composition preferentially. The nature of the filter selected depends upon the characteristics of the tracer and the liquid components of the composition. Suitable filters include those made from PTFE. The non-affinity of a proposed filter medium for the tracer compound can be tested by passing a solution containing the tracer compound in a solvent through the filter medium and determining whether the SES signal is changed after filtration. Without wishing to be bound, we believe that the presence of certain solids may adsorb or absorb tracer or otherwise interfere with the binding of tracer molecules to a spectroscopy-enhancing surface. In addition the presence of solids may adversely affect the aggregation of colloidal metal SES substrates, which usually require aggregation in order to produce SES effects, or the transmission of light through the sample.

In some embodiments of the method of the invention, the sample may be diluted with a diluent liquid. Dilution of the liquid may be carried out before or after the optional separation step, if done. We have found that dilution of the composition by mixing with a liquid may enhance the SES spectrum of the tracer compound compared with an undiluted sample, possibly because spectra from other components of the composition are suppressed. Dilution of the sample also facilitates the accurate handling and dispensing of viscous samples. Clearly, the amount of liquid used to dilute the sample must be known in order to calculate the concentration of the tracer compound in the original sample before dilution. The diluent liquid is preferably miscible with at least some of the components of the composition. For many compositions, water may be used as a diluent. The sample may be diluted by any suitable amount required to increase the SES spectrum and/or improve the accuracy of dispensing the sample. The identity and optimal amount of a suitable diluent to be used may be determined by routine experimentation. Typically the sample is diluted to about 1-1000 times by volume or by weight, especially about 10-20 times. In some circumstances, it may be more convenient to dilute by weight if accurate dispensing of a volume is difficult due to the viscosity of a composition.

The SES substrate is a substrate having a surface which is capable of enhancing the spectroscopic response of a molecule which is close to or in contact with the surface, i.e. it is capable of promoting surface-enhanced spectroscopy. The SES substrate may be any material capable of enhancing spectroscopy, in particular vibrational and Raman spectroscopy. SES substrates typically comprise metals such as silver, gold and copper. The use of other SES substrates, particularly metals, may be possible, including Na and Al and transition metals such as Pt, Ni, Ru, Rh, Pd, Co, Fe, Cr. As new methods of surface-enhanced spectroscopy are developed, different SES-promoting substrates may become available and may be useful for the method of the invention. The SES substrate may take the form of small particles, usually nanoparticles, typically used as colloidal solutions, especially aqueous colloidal solutions. Alternatively the SES substrate may take the form of a planar material having a metallic surface comprising microstructure in the form of an immobilised metal colloid or a patterned surface made from or coated with a metal such as gold, silver or copper. Suitable SES substrates are widely available commercially, either as colloidal gold, silver or copper solutions or as specialist planar materials for SES having plasmonic surfaces, such as Klarite™. As a further alternative, the SES substrate may comprise a SES membrane or coating such as iFyber™, which is an absorbent membrane coated with gold or silver nanoparticles. Other nanoparticle-coated substrates may also be used, such as fibres or silica or glass spheres.

In a preferred form, the spectroscopy-enhancing surface comprises colloidal nanoparticles of gold, silver or copper dispersed in a liquid, which is usually an aqueous liquid. Typically, the liquid sample, after it has been separated from any solids present in the original composition, is added to the colloidal solution of metal particles, or vice versa, and agitated to bring the compounds present in the liquid sample into contact with the metal particles. It is well-known that the spectroscopy-enhancing effect of metal nanoparticles is increased when the nanoparticles are aggregated into clusters. An aggregating agent is preferably added to the mixture of colloidal particles and the liquid in order to promote aggregation of the metal particles to increase the spectroscopy-enhancing effect of the metal surfaces. We have found that the selection of a particular aggregating agent may promote the SES signal obtained from the sample. The aggregating agent may be added to the liquid before or after it is mixed with colloidal nanoparticles. It has been found to be beneficial in some circumstances to add the aggregating agent after the liquid sample has been mixed with the colloidal particles, in particular because the method may be made more reproducible thereby. Aggregating agents may be selected from acids, such as HCl, $HNO_3$ for example, and bases, such as organic amines for example, and salt solutions, e.g. metal chlorides, nitrates or sulphates, amongst others. In addition to the selection of a particular compound as aggregating agent, we have found that the concentration of the aggregating agent and/or the amount of aggregating agent used may also have a marked effect on the intensity of the SES signal obtained from a sample in a colloidal metal mixture. It is known that detection of some modes of Raman scattering are enhanced using SES relative to other modes. Preferably the SES substrate and aggregating agent (if used) is selected so that selective bands or peaks of the tracer are enhanced to further increase the signal obtained from low tracer concentrations.

The concentration of the tracer in the sample is calculated relative to the concentration of at least one original liquid ingredient of the composition.

The at least one original liquid ingredient may be the principal or sole ingredient of the composition, for example, in the case of a liquid fuel composition the original liquid ingredient may be the fuel compound itself. When the liquid composition contains more than one ingredient, the original liquid ingredient may be any one of those ingredients. The original liquid ingredient may be a dissolved form of a compound which would be a solid but for its inclusion in a liquid composition. The term original liquid ingredient is not intended to include a tracer compound, i.e. a compound added to the composition solely for the purpose of identification. The original liquid ingredient is not intended to and preferably does not include liquid compounds added to the composition for the purposes of analysis, such as solvents required for analytical purposes or internal standards. The original liquid ingredient is a component of the liquid composition at the time the tracer is added to the composition. The original liquid ingredient is susceptible to be detected by means of SES.

Preferably, the original liquid ingredient is a functional ingredient of the composition. By functional ingredient, we mean a compound which is present in the composition for a purpose related to the intended use of the composition, in contrast to a tracer compound which is added to the composition for the purpose of identification and which usually does not contribute to the intended use of the composition. The functional ingredient may be an active compound, such as a biocidal compound in a pesticide composition or urea in a diesel exhaust additive for example, or an auxiliary ingredient such as a preservative, anti-foam, solvent, surfactant, diluent, colourant, perfume or other compound having a role in the composition related to the physical incorporation of the active compound in the composition or the enhancement and prolongation of its activity. When the concentration of the tracer is calculated relative to an original liquid ingredient, it is not necessary to calculate its absolute concentration in the composition. The original liquid ingredient preferably yields a SES spectrum using the method of the invention and preferably yields measurable but distinct peaks in the same SES spectrum as the tracer compound. It is preferred that the SES substrate, aggregating agent (if used) and conditions of analysis are selected such that the SES spectrum yields a clear spectrum showing distinct and measurable peaks associated with the tracer compound and also distinct and measurable peaks associated with the original liquid ingredient. Preferably the SES substrate and aggregating agent (if used) is selected so that selective bands or peaks of the tracer are enhanced to further increase the signal obtained from low tracer concentrations. In such a case it may only be necessary to calculate the ratio of the intensity of a single peak associated with the tracer to that of one or more peaks associated with the original liquid ingredient in the spectrum acquired using the method of the invention. More than one peak of the tracer and original liquid ingredient may be compared and used to calculate a relative concentration of the tracer. As a further alternative, a characteristic of the combined spectrum of the tracer and original liquid ingredient may be used as an indication of the concentration of the tracer in the composition. The intensity or another characteristic of one or more peaks associated with the tracer occurring in an SES spectrum may be compared to a characteristic of one or more peaks associated with the original liquid ingredient in a spectrum acquired using a similar or a different spectroscopic method. The different spectroscopic method may be an SES method which differs from the method used to obtain the spectrum of the tracer compound. Alternatively it may be a non-SES method such as infra-red spectroscopy or non-SES Raman spectroscopy, for example.

The relative amount of the SERS-active tracer compound and the original liquid ingredient may be calculated from the ratio of (i) the Raman spectroscopy detector response to the SERS-active tracer compound to (ii) the spectroscopy detector response to the original liquid ingredient. The detector response ratio may be the ratio of selected peaks (peak height, peak area) of the SES spectrum and a non-SES spectrum, if used. The SES spectrum obtained from a reference sample containing only the target SES-active tracer or the original liquid ingredient may be used to identify suitable peaks which are characteristic of either the tracer or the original liquid ingredient, which may be selected for comparing the relative response of the compounds. The relative response may be calculated from the relative intensity of one peak attributable to each compound or from more than one peak. As an alternative, the whole spectrum, or a portion of it, obtained from the Raman spectroscopy of the sample in contact with the SES substrate may be compared, preferably in vector form, to a spectrum obtained from a reference sample containing a known concentration of the SES-active tracer compound in contact with the SES substrate and a spectrum obtained from a reference sample containing a known concentration of the original liquid ingredient in contact with the SERS substrate. A calculated property of the spectrum, such as the relative response compared to a reference spectrum of one or each compound present may be used to represent the detector response due to the SERS-active tracer and/or the original liquid ingredient. It is not always necessary to collect and display a Raman spectrum. It may be sufficient to measure the detector response at one or more predetermined Raman shift wavenumbers or ranges of wavenumbers and calculate a concentration of the tracer from the measured response. The result of the calculation may be displayed to the user as a concentration value, a "pass/fail" result or as an arbitrary value of quality or similarity based upon a value for a solution containing a standard amount of the tracer. Methods of comparing spectra and calculating relative response and peak ratios are well-known and are typically carried out using a suitable computer programmed with spectroscopic data handling software. The relationship between the concentration of the SERS-active tracer compound and the Raman detector response ratio is linear and may be determined by calibration.

The method of the invention may be carried out quickly and with the use of compact equipment and so it may be used as a test to confirm the identity of a composition "in the field" where the composition is sold, transported or stored. If required a confirmatory analysis may be carried out using standard laboratory methods such as chromatography and mass-spectrometry in order to confirm the result obtained by the method of the invention. The confirmatory analysis may measure the concentration of the tracer or of another component of the composition, such as a second tracer or a functional ingredient of the composition.

DETAILED DESCRIPTION OF THE INVENTION

Example 1

130 μl of silver colloid and 130 μl of highly pure water was added to a well (of a 96-well plate) and thoroughly mixed. A 30 µl sample of a tagged pesticide containing 100 ppb w/v ($10^{-7}$M) of a tracer compound was added to the well. The contents of the well plate were thoroughly mixed by pipette aspiration. Then 10 µl of 0.01 M spermine was added to the mixture and mixed. SERS measurement was then performed on the sample using a Renishaw™ inVia Raman Microscope using a 5× objective, at 532 nm excitation wavelength.

Figure 1:
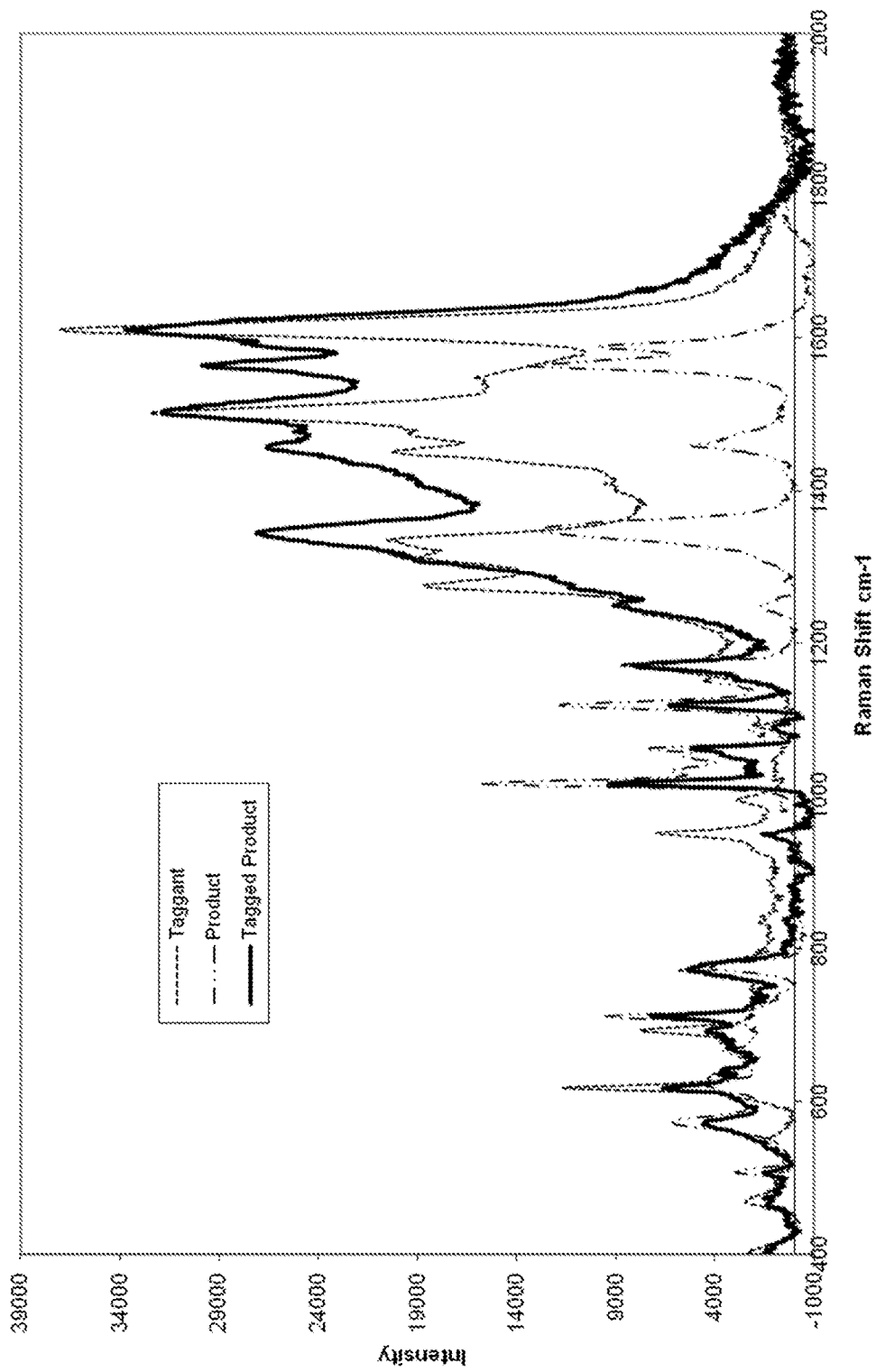
FIG. 1 is a Raman spectrum for the tracer, product and tracer-product mixture described in Example 1.

The Raman spectrum obtained from the sample is shown in FIG. 1 as the bold line of the spectrum. Also shown in FIG. 1 for comparison are spectra of the tracer compound in water (dashed line) and the untagged pesticide product (dot-dashed line).

Comparing the spectra, it is clear that there are several peaks in the tagged product spectrum which are attributable either to the tracer or the product and that these peaks can be used to determine the relative amount of tracer in the product.

Example 2

A Raman active tracer compound, selected from the current list of compounds approved for addition to foods, was used to tag a commercially available agrochemical formulation. A solution containing 100 mg/l of the Raman active tracer compound was prepared in deionised water. Portions of this solution were used to tag samples of an agrochemical product at concentrations of the Raman active compound in the agrochemical formulation ranging from 0 mg/l to 5 mg/l.

Samples of the tagged and untagged agrochemical product were diluted to at least ¹/₁₀ concentration with deionised water prior to analysis. The diluted agrochemical product (<10 microliters) was added to water (130 microliters) in a 2 ml screw top glass vial. Silver colloid (130 microliters) was added and then spermine (10 microliters, 0.01 M) was also added as an aggregating agent. The vial was agitated thoroughly. Raman spectra were acquired on a Sierra 532 nm Raman spectrometer from Snowy Range Instruments Inc, with a 0.5 second acquisition time, averaged over 50 scans at 40 mW laser power.

Figure 2:
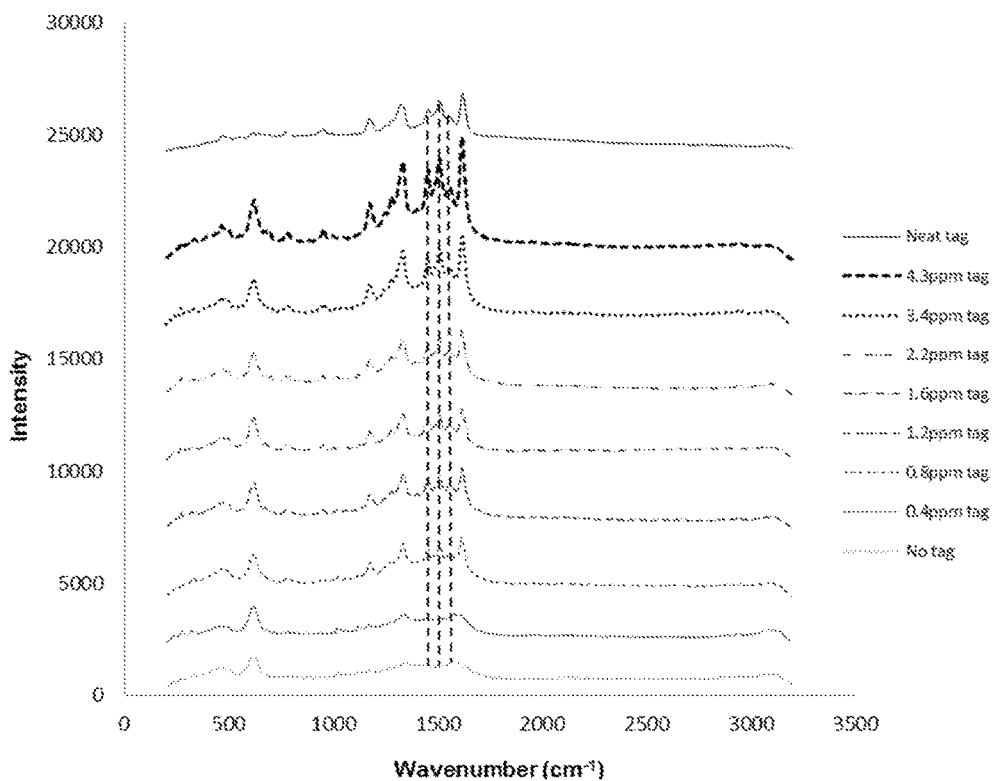
FIG. 2 is a Raman spectrum for the tracer, product and tracer-product mixture described in Example 2.

The spectrum of the untagged agrochemical product was obtained and the position of its Raman signals noted. Spectra of the tagged agrochemical products were also obtained and those signals arising from the tracer were noted. The vertical lines in FIG. 2 show the position of the tracer signals in the spectra (if present). The spectra have been artificially off-set from one another for illustrative purposes.

Figure 3:
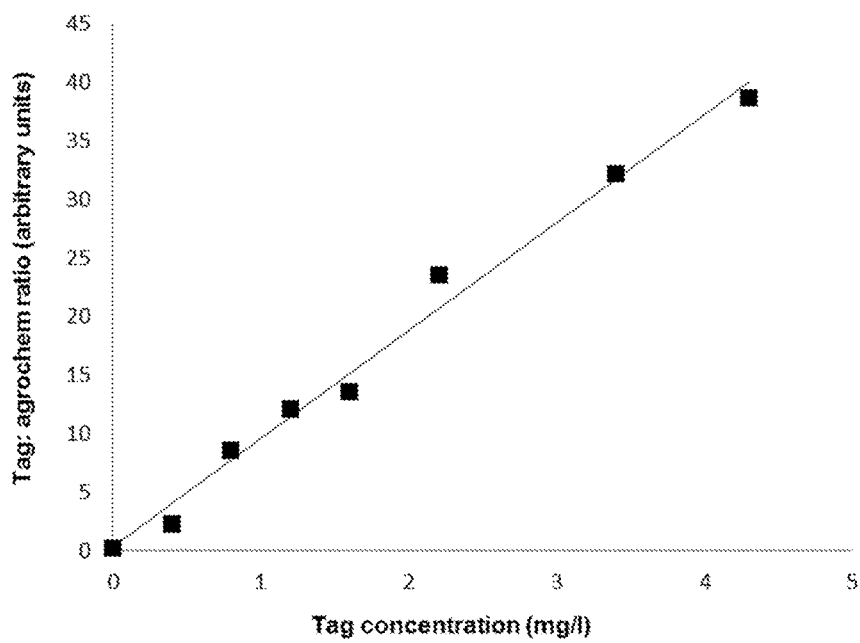
FIG. 3 is a plot of tracer concentration vs SES response ratio of the original liquid ingredient and tracer of Example 2.

The ratio of the height of a peak from the tracer to the height of a peak from the agrochemical product is plotted as a function of tracer concentration in FIG. 3. The ratio varies linearly with the concentration of the tracer. Knowing the relationship between the signal ratio and tracer concentration, the operator has a means of establishing the concentration of tracer in a sample of agrochemical product of uncertain provenance.

Example 3

A Raman active tracer compound was used to tag a commercially available matte white paint. A solution containing 4 mg/l of the Raman active compound was prepared in deionised water. Portions of this solution were used to tag samples of paint at concentrations of the Raman active compound in the paint ranging from 0 mg/l to 50 mg/l.

Prior to analysis, the sample of paint under test was diluted to ¹/₁₀ concentration with deionised water. The diluted paint (30 microliters) was added to 90 nm colloidal gold (500 microliters, 0.01% w/vol) in a 2 ml screw top glass vial. This was agitated thoroughly and salt solution (500 microliters, 10% w/vol) was then added. The sample was centrifuged for five minutes at 2500 rpm. Raman spectra were acquired on a 785 nm QE65000 Raman spectrometer from Ocean Optics Inc with a 1 second acquisition time and laser power of 180 mW.

Figure 4:
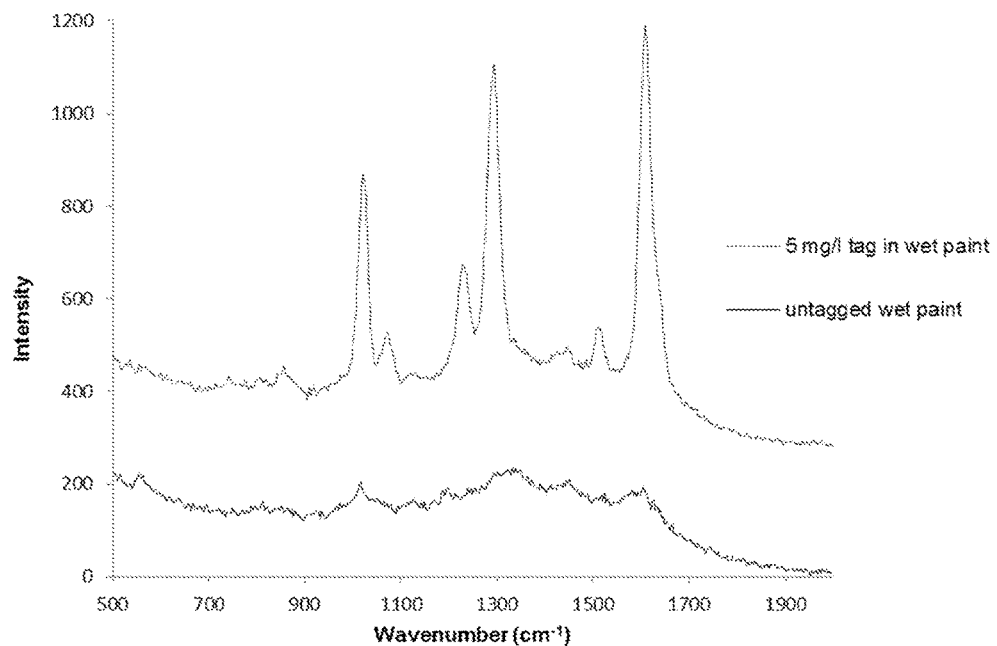
FIG. 4 is a Raman spectrum for the tracer, product and tracer-product mixture described in Example 3.
Figure 5:
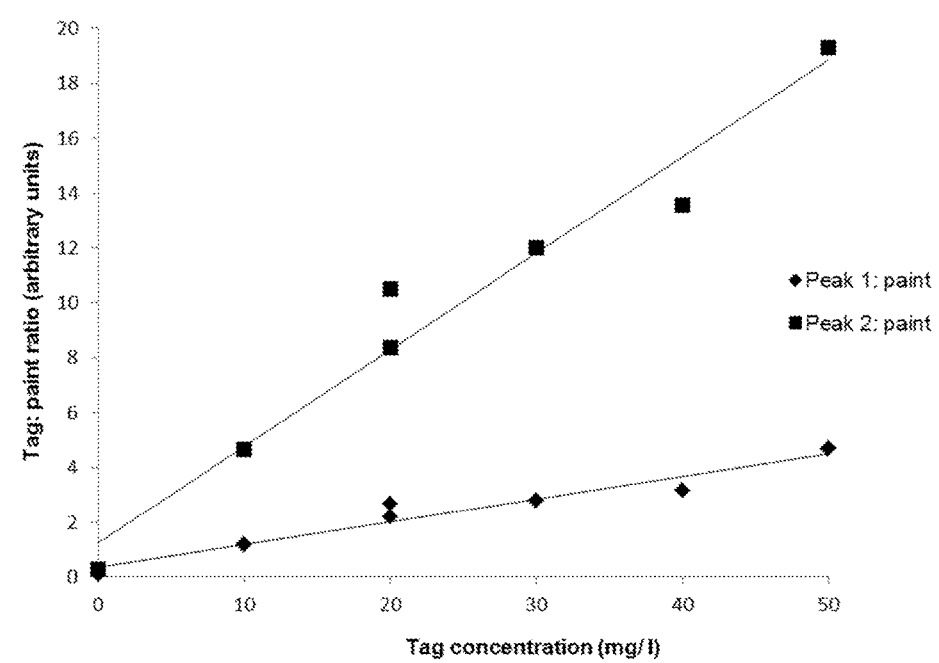
FIG. 5 is a plot of tracer concentration vs SES response ratio of the original liquid ingredient and tracer of Example 3.
Figure 6:
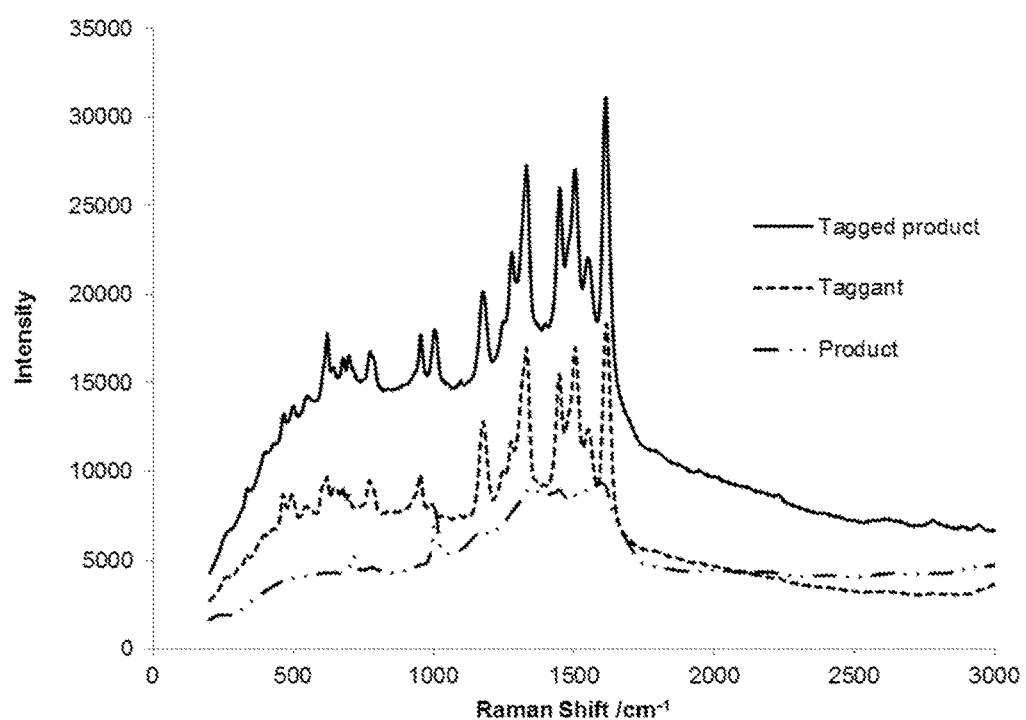
FIG. 6 is a Raman spectrum for the tracer, product and tracer-product mixture described in Example 4.

FIG. 4 compares the Raman spectrum of tagged and untagged paint. The ratio of the height of two peaks from the tracer each in relation to a peak from the paint (outside the wavenumber range shown in FIG. 4) is plotted as a function of tracer concentration in FIG. 5. The ratio of signals varies linearly with the concentration of the tracer. Knowing the relationship between the ratio of signals and tracer concentration, the operator has a means of establishing the concentration of tracer in a sample of paint of uncertain provenance.

Example 4

A sample of diesel exhaust fluid containing 32.5% by weight of urea in aqueous solution was the product to be tagged. A Raman active tracer compound was added to the diesel exhaust fluid so as to give a final concentration of tracer of $1.1 \times 10^{-6}$M. The diesel exhaust fluid was used in subsequent analysis without any prior dilution.

The tagged diesel exhaust fluid (30 microliters) was added to water (130 microliters) in a 2 ml screw top glass vial. Silver colloid (130 microliters) was then added and the contents mixed by sonication (15 min). Spermine (10 microliters, 0.01 M) was added to the mixture and the vial mixed again by sonication. Raman spectra were acquired on a Sierra 532 nm Raman spectrometer from Snowy Range Instruments™ Inc, with a 0.5 second acquisition time, averaged over 10 scans at 40 mW laser power.

The Raman spectrum of the untagged diesel exhaust fluid was obtained and the position of its Raman signals noted. The spectrum of the tagged diesel exhaust fluid was also obtained and those signals arising from the tracer were noted.

The ratio of a peak from the tracer and a peak from the diesel exhaust fluid could be interpreted so as to ascertain the amount of tracer in the sample. Knowing the relationship between the ratio of tracer to urea signal and tracer concentration, the operator has a means of establishing the concentration of tracer in a sample of diesel exhaust fluid of uncertain provenance.

The invention claimed is:

1. A method of identifying a liquid composition comprising at least one original liquid ingredient, said method comprising the steps of:
   a. adding a tracer compound to a known liquid composition containing said at least one original liquid ingredient so as to dissolve the tracer in the known liquid composition and form a tagged known liquid composition;
   b. obtaining a sample of an unidentified liquid composition,
   c. contacting said sample of the unidentified liquid composition with a spectroscopy-enhancing surface comprising gold, silver or copper;
   d. obtaining at least one Raman spectrum from the sample of the unidentified liquid composition; and
   e. calculating, from said spectrum, the concentration of the dissolved tracer relative to the concentration of said original liquid ingredient in the sample of the unidentified liquid composition; and f. comparing the relative concentration calculated in step e with the corresponding relative concentration of the dissolved tracer and original liquid ingredient of the tagged known liquid composition, wherein the original liquid ingredient comprises a functional ingredient of the composition and the original liquid ingredient is not the dissolved tracer compound.

2. The method according to claim 1, wherein the at least one Raman spectrum is a resonance Raman spectrum.

3. The method according to claim 1, wherein the concentration of said original liquid ingredient is estimated by a spectroscopic method.

4. The method according to claim 3, wherein said calculation comprises the step of comparing at least one characteristic of a first peak in a spectrum attributed to the tracer compound with at least one characteristic of a second peak in a spectrum attributed to said original liquid ingredient.

5. The method according to claim 4, wherein the first and second peaks occur in the same spectrum.

6. The method according to claim 4, wherein the first and second peaks occur in first and second spectra which are different spectra.

7. The method according to claim 6, wherein said first and second spectra are obtained using the same spectroscopy method.

8. The method according to claim 6, wherein said first and second spectra are obtained using different spectroscopy methods.

9. The method according to claim 1, wherein the liquid composition to be identified comprises a fuel, fuel additive, lubricant, biologically derived product, diesel exhaust fluid, pesticide, paint, ink or medicine.

10. The method according to claim 1, wherein the sample of an unidentified liquid composition is separated into a solids portion and a liquid portion prior to step c.

11. The method according to claim 1, wherein an
aggregating agent is added to the sample of unidentified liquid composition prior to, during or immediately after step c.

12. The method according to claim 2, wherein the concentration of said original liquid ingredient is estimated by a spectroscopic method.

13. The method according to claim 1, wherein the sample of an unidentified liquid composition obtained in step b is diluted by mixing with a liquid to provide a diluted sample of an unidentified liquid composition and said diluted sample of an unidentified liquid composition is contacted with a spectroscopy-enhancing surface comprising gold, silver or copper in step c.

* * * * *